United States Patent
Airaksinen et al.

(10) Patent No.: US 8,192,629 B2
(45) Date of Patent: *Jun. 5, 2012

(54) SEPARATION PROCESS

(75) Inventors: Jyrki Airaksinen, Espoo (FI); Heikki Heikkilä, Espoo (FI); Jari Lewandowski, Siuntio (FI); Kari Laiho, Kirkkonummi (FI)

(73) Assignee: Danisco A/S, Copenhagen K (DK)

( * ) Notice: Subject to any disclaimer, the term of this patent is extended or adjusted under 35 U.S.C. 154(b) by 289 days.

This patent is subject to a terminal disclaimer.

(21) Appl. No.: 12/711,547

(22) Filed: Feb. 24, 2010

(65) Prior Publication Data

US 2010/0212662 A1    Aug. 26, 2010

Related U.S. Application Data

(60) Provisional application No. 61/155,261, filed on Feb. 25, 2009.

(51) Int. Cl.
*B01D 15/08* (2006.01)
(52) U.S. Cl. ..... 210/659; 210/635; 210/656; 210/198.2; 127/46.2; 127/46.3
(58) Field of Classification Search .......... 210/635, 210/656, 659, 198.2; 127/46.2, 46.3, 55
See application file for complete search history.

(56) References Cited

U.S. PATENT DOCUMENTS

| | | | |
|---|---|---|---|
| 4,109,075 | A | 8/1978 | Deaton |
| 4,182,633 | A | 1/1980 | Ishikawa et al. |
| 4,267,054 | A | 5/1981 | Yoritomi et al. |
| 4,402,832 | A | 9/1983 | Gerhold |
| 4,487,198 | A | 12/1984 | Miyake et al. |
| 4,843,156 | A | 6/1989 | Miyake et al. |
| 5,127,957 | A | 7/1992 | Heikkila et al. |
| 6,093,326 | A | 7/2000 | Heikkila et al. |
| 6,200,390 | B1 | 3/2001 | Kearney et al. |
| 6,224,776 | B1 | 5/2001 | Heikkila et al. |
| 6,602,420 | B2 | 8/2003 | Kearney et al. |
| 6,685,781 | B2 | 2/2004 | Hyöky et al. |
| 6,896,811 | B2 | 5/2005 | Heikkila et al. |
| 7,959,811 | B2 * | 6/2011 | Airaksinen et al. .......... 210/659 |
| 2003/0173299 | A1 * | 9/2003 | Heikkila et al. ............. 210/656 |
| 2010/0212662 | A1 * | 8/2010 | Airaksinen et al. ............ 127/42 |

OTHER PUBLICATIONS

International Search Report and Written Opinion dated May 28, 2010 issued in respect to corresponding International Application No. PCT/FI2010/050127.

* cited by examiner

*Primary Examiner* — Ernest G Therkorn
(74) *Attorney, Agent, or Firm* — Scully, Scott, Murphy & Presser, P.C.

(57) ABSTRACT

The present invention relates to a chromatographic separation process for fractionating betaine-containing solutions by utilizing fractions comprising parts of the separation profile as a substituent of the eluent in a novel and inventive manner. The process provides improved separation capacity and separation efficiency without affecting the yield or purity of betaine or other products. The process can especially be applied to sequential SMB separation systems.

33 Claims, 2 Drawing Sheets

FIGURE 2.

SEPARATION PROCESS

CROSS-REFERENCE TO RELATED APPLICATIONS

This application claims the benefit of U.S. Provisional Application No. 61/155,261 filed on Feb. 25, 2009.

FIELD OF THE INVENTION

The present invention relates to the field of chromatographic separation and especially to chromatographic fractionation of betaine-containing solutions by simulated moving bed and batch methods. The process of the invention aims at improving the separation efficiency of the separation system by introducing fractions comprising parts of the separation profile back to the separation system in a novel and inventive manner to decrease the volume of the fresh eluent while essentially maintaining or even improving the yield and/or purity of betaine or other products.

BACKGROUND OF THE INVENTION

Chromatographic separation systems for separating betaine and other components from betaine-containing plant-based solutions have been developed in recent years to improve the separation capacity and the separation efficiency of the systems. However, especially chromatographic SMB separation systems have the drawback that the ratio of eluent to feed has conventionally been rather high owing to the very complex nature of the SMB systems. Various arrangements for circulating fractions of the eluate back to the separation system are already in use in chromatographic SMB systems.

U.S. Pat. No. 4,109,075 (CPC International Inc.) discloses a process for separating saccharides for example from a starch conversion product by a batch chromatography method, wherein at least three different saccharide fractions with differing molecular weight are collected. The first saccharide fraction (the highest molecular weight fraction) is then used for elution of the next feed, followed by elution with water. It is recited that this mode of operation minimizes the amount of eluent water and produces fractions rich in any one of lower saccharides $DP_1$ through $DP_4$.

U.S. Pat. No. 4,267,054 (Sanmatsu Kogyo Co.) discloses a batch chromatographic separation process for separating two components (such as glucose and fructose) from a multicomponent mixture, where the eluate coming from the separation column is collected in four fractions (a), b), (c) and (d). Fractions (a) and (c) are product fractions, fraction (b) is a mixed fraction containing relatively large amounts of the target products and fraction (d) comprises a dilute fraction of the tail of fraction (c) and the head of fraction (a) used in the next cycle of operation. Fractions (b) and (d) are returned to the separation system by introducing them to the top of the separation column.

U.S. Pat. No. 4,402,832 (UOP Inc.) discloses a process for separating an extract component (such as fructose) from a raffinate component (such as glucose) in an SMB chromatographic system, where a dilute extract fraction and an impure raffinate fraction are returned to the same column from which they are collected. It is recited that the process provides considerable savings in the energy required to recover the eluent from the product streams as compared to prior art processes. Furthermore, it is recited that a reduced rate of fluid circulation through the separating units is achieved, which enables denser packing of the columns. This, in turn, is recited to minimize channeling through the adsorbent bed and to minimize void volume.

U.S. Pat. No. 4,487,198 (Hayashibara) discloses a dual stage batch process for separating maltose from sugar starch solutions, where the eluate coming from the separation column in the first stage is collected in five fractions A, B, C, D and E. Fraction A is a dextrin fraction, fraction C is a maltose fraction and fraction E is a glucose fraction. Fraction B is a rear slope fraction containing dextrin with maltose impurities, and fraction D is a front slope fraction containing maltose with glucose impurities. In the next stage, fractions B and D are sequentially in this order applied to the separation column together with a fresh feed so that fraction B is introduced before the feed and fraction D after the feed.

U.S. Pat. No. 6,200,390 B1 (Amalgamated Research Inc.) discloses a continuous SMB process for recovering betaine and sugars from molasses, for example. In this process, a "block" of betaine is displaced from the circulation loop of the SMB system without disturbing the normal operation of the system. In practice, a betaine-concentrated fraction is withdrawn from the circulation loop of the continuous SMB system while an equal volume of water is introduced to the circulation loop. The circulation loop then continues without disruption.

U.S. Pat. No. 6,602,420 B2 (Amalgamated Research Inc.) discloses a two-step chromatographic separation process with coupled looping, including a simulated moving bed operation coupled with continuous displacement chromatography (continuous SMB). The process may be applied to the recovery of betaine and/or invert sugar from sucrose solutions, such as molasses, to enable the subsequent production of a high purity sucrose product. It is recited that the use of displacement rather than elution provides reduction in the quantity of the eluent. It is stated that typical molasses chromatographic separation systems use ratios of about 6.0 to 8.0 water volume for each volume of feed molasses (60% dissolved solids in the feed), whereas the application of displacement chromatography permits organic compounds (such as betaine) to be separated with water-to-feed ratios of 2.0 or less. Furthermore, the concentration of the betaine fraction is recited to rise from a typical range of 1 to 5% dissolved solids to a range of 8 to 15% dissolved solids.

U.S. Pat. No. 5,127,957 (Heikkilä et al.) discloses a sequential SMB method having at least three columns for separating betaine, sucrose and rest molasses from molasses during the same cycle (one loop). In one embodiment of the process, a new portion of feed solution is added to the column series between partly separated rest molasses and sucrose fractions to the top of a preselected column.

U.S. Pat. No. 6,093,326 (Danisco Finland Oy) discloses a two-loop SMB method comprising at least two packing material beds for processing a beet molasses based solution to recover a betaine fraction and a sucrose fraction.

U.S. Pat. No. 6,896,811 B2 (Danisco Sweeteners Oy) discloses an SMB method for fractionating a solution into at least two fractions by circulating the formed separation profile more than once or less than once through the chromatographic separation loop during one cycle (before the next feed is supplied to the separation system).

It appears from the above-described prior art that it is known to return fractions comprising different parts of the separation profile back to the separation columns. It also appears that the known arrangements provide reduced amounts of the eluent, savings in the energy required to recover the eluent from the product streams, as well as higher purities of target component fractions. However, a need still exists for a more versatile separation process, where parts of the separation profile containing different fast moving and slow moving components are introduced back to different positions of the separation system as an eluent substitute to reduce further concentration costs and to enable the recovery of the components in desired target fractions while essentially maintaining or even improving the yield and purity of the product components.

DEFINITIONS RELATING TO THE INVENTION

"A product fraction" is a fraction taken out of the chromatographic separation process and comprising product components. There can be one or more product fractions.

"A residue fraction" or "a residual fraction" is a fraction which mainly contains components (such as salts, color compounds, organic acids, amino acids, etc.) other than the product components, which are recovered. There can be one or more residue fractions. The components of the residual fraction are also referred to as "residual components".

"A recycle fraction" is a fraction, which contains incompletely separated product compounds, which has a lower purity than the product fractions and which is recycled back to the separation to be combined with the feed. The recycle fraction is typically used as a diluent of the feed. There may also be one or more operations before returning the recycle to the column(s); for example, the recycle fraction(s) may be concentrated by evaporation. There can be one or more recycle fractions.

"A sucrose recycle fraction" refers to a recycle fraction which is a part of the sucrose subprofile. In connection with the present invention, the sucrose recycle fraction is especially a front slope part or a rear slope part of a sucrose subprofile.

"A sequence" or "a separation sequence" is a predetermined sequence of steps which are continuously repeated in a sequential chromatographic separation process, comprising all steps that are required to facilitate the separation of feed components to product fraction(s) and other fractions.

"A step" comprises one or more of a feeding phase, an elution phase and a circulation phase.

During the feeding phase, a feed solution is introduced into a predetermined partial packed bed or predetermined partial packed beds. During the feeding phase, and/or one or more other phases, one or more product fractions and one or more residual fractions can be withdrawn.

During the elution phase, an eluent is fed into predetermined partial packed beds.

During the circulation phase, essentially no feed solution or eluent is supplied to the partial packed beds and no products are withdrawn.

"SMB" refers to a simulated moving bed system.

In a continuous SMB system, all the fluid streams flow continuously. These streams are: the supply of a feed solution and an eluent, circulation of the separation profile and withdrawal of the products.

In a sequential SMB system, not all of the fluid streams (defined above) flow continuously.

"A feed" is an amount of feed solution introduced to the separation column during one sequence.

"A subprofile" is a concentration profile of one component, also named as the component peak.

"A separation profile" refers to a dry solids profile formed from the dissolved substances (DS) present in the feed on account of the feed of eluent and feed solution and the flow through the packing material bed in a separation column, obtained by accomplishing/repeating the separation sequence.

"A part of the separation profile" refers to any section of the separation profile which contains liquid and components in this section and which is used as an eluent replacement. Equal to "part" or "PART".

"A part feeding phase" refers to the introduction of the part to the separation system as an eluent replacement.

"A peak" is the part of the chromatogram where a detector response is caused by a component.

"A retention volume" (Rt) is the volume of the mobile phase required to elute a component or a certain point of the separation profile through a resin bed. The retention volume of a component may be expressed as % of the resin bed volume. In connection with the present invention, a retention volume especially refers to the volume required to elute the start of a component peak (such as a betaine peak) through the column.

"Tailing" refers to the phenomenon in which the normal Gaussian peak has an asymmetry factor >1. Tailing is most often caused by sites on the packing that have a stronger than normal retention for the solute.

"A void" or "void volume" in connection with the present invention refers to the volume required to elute the start of the conductivity peak (salts) through the column.

"BV" refers to the resin bed volume of columns, partial packed beds or a separation system.

"Peak broadening" refers to the dispersion, of a chromatographic peak (separation profile) as it moves through the column.

"Volume of steps" (V) refers to the volume of the mobile phase (including the feed, eluent and circulation) which moves a component, a separation profile or parts thereof through the separation column(s) from a predetermined step in a separation sequence to another predetermined step in the same or following sequences. The volume of steps is calculated step by step by summing up the volumes of the mobile phase transferred in each step (the volume introduced to the columns in each step during the feeding, elution and/or circulation phases).

"An eluent introduction position" refers to any location in the chromatographic system where an eluent may be introduced.

"DS" refers to the dissolved dry substance content. Equal to "dissolved solids content".

"Purity of a component" refers to the content of the component on DS.

"Separation capacity" refers to the amount of a product (kg)/volume of separation resin ($m^3$)/hour (h). Recycle is not included.

BRIEF DESCRIPTION OF THE INVENTION

The present invention provides a process for fractionating betaine-containing solutions in a chromatographic separation system by using parts of the separation profile from the separation as a substitute for the eluent. It is also essential that said parts with their components are directed to a correct position in a correct step in the separation system so that the components contained therein end up into suitable fractions while essentially maintaining or even improving the purity of the product fractions, the yield of the product components and the separation capacity. The objects of the invention are achieved by a process which is characterized by what is stated in the independent claims. Preferred embodiments of the invention are disclosed in the dependent claims.

It was surprising to find out that said parts as a substitute for the eluent and containing different fast moving and/or slow moving components did not disturb the separation efficiency of the separation system. Furthermore, the volume of fresh eluent could be reduced for example in an amount of 10% to 70% from that used in the prior art. The process also provided a higher solids content of the fraction(s) to be withdrawn, which leads to a reduced energy requirement in subsequent concentration stages. The evaporation need for concentration of residue fractions, for example, may be reduced by an amount of 5 to 50% or even more.

BRIEF DESCRIPTION OF THE DRAWINGS

FIGS. 1 and 2 relate to sequential SMB separation of beet molasses described in Example 2 (4-column set, 2-profile mode).

DETAILED DESCRIPTION OF THE INVENTION

The present invention relates to a process for fractionating a betaine-containing solution in a chromatographic separation system, which comprises one or more columns containing one or more partial packed beds, comprising feeding the betaine-containing solution into the separation system, introducing an eluent into the separation system to elute components of the betaine-containing solution to form a separation profile, and recovering a betaine product fraction, one or more residual fractions and optionally one or more recycle fractions and one or more other product fractions.

The process of the present invention is characterized by introducing one or more parts of the separation profile to one or more eluent introduction positions of the separation system in one or more part feeding phases to substitute a portion of the eluent, said parts comprising one or more components selected from betaine, one or more other product components, and one or more residual components, moving said parts with their components forward in the separation system by using a sequence of steps, which steps comprise one or more of a feeding phase, a circulation phase and an elution phase, and withdrawing components of said parts during the same or following separation sequences in one or more residual fractions and/or in one or more recycle fractions and/or in one or more product fractions, whereby the volume, introduction position and introduction step of said parts are determined on the basis of the retention volumes of the components of said parts, the volume of the resin bed through which the components of the parts pass and the volume of the steps moving the components of the parts from the introduction position to the calculated target withdrawal position of the components during said same or following separation sequences while essentially maintaining or improving the purity of the product fraction(s) and the yield of the product components.

The chromatographic separation system of the present invention comprises one or more separation columns containing one or more partial packed beds. The partial packed beds are composed of chromatographic separation resin, which forms the resin bed of the system. The columns/partial packed beds may form one or more loops. During the separation process, the dissolved substances present in the feed, together with the eluent, are moved forward and separated in the partial packed beds of the separation column(s), resulting in the formation of a separation profile. A betaine product fraction, one or more residual fractions and also generally one or more recycle fractions, and one or more other product fractions are recovered.

In the process of the present invention, one or more parts of the separation profile thus formed are introduced to one or more eluent introduction positions in one or more part feeding phases to substitute a portion of the eluent. Said part may be introduced to substitute the eluent at the beginning, in the middle or at the end of an elution phase.

In the following description of the invention, for the sake of convenience, said one or more parts of the separation profile are also referred to as "parts of the separation profile" or "parts".

Said parts may be introduced into any column or any part of a column whereto an eluent is introduced.

Said parts of the separation profile may comprise one or more components selected from betaine, one or more other product components and one or more residual components. In betaine-containing solutions of the present invention, said parts typically contain components selected from betaine, sucrose, salts, organic acids and salts thereof, amino acids, and glycerol.

Said parts may contain fast-moving and/or slow-moving components. Salts represent an example of the fast-moving components. Organic acids and sucrose as a rule move faster than betaine.

In molasses separation, said parts may be a front and/or rear slope of the subprofiles of betaine, sucrose or residual components. Said parts are typically front slope and/or rear slope portions of a betaine subprofile and one or more different front slope portions of a residual subprofile.

In the process of the present invention, said parts with their components are moved forward in the separation system by using a sequence of steps, which steps comprise one or more of a feeding phase, a circulation phase, and an elution phase.

In the sequential separation system, several of said parts originating from different parts of the separation profile may be used as an eluent during one sequence. The number of said parts may be 1 to 5, they may differ from one another, and they are introduced as an eluent into various positions of the system either as collected fractions or transferred as an intact profile.

Withdrawal of components of said parts during the same or following separation sequences may be carried out in residual fraction(s), recycle fraction(s) and/or product fraction(s) directly or after an intermediate stage.

Moving of the components of said parts in the separation system may proceed through intermediate stages before the final withdrawal thereof. Intermediate stages are untypical fractions or positions in the separation profile, where the component(s) is/are directed to be reintroduced back to the separation system for the final separation and withdrawal thereof or to be reintroduced to a distinct separation system.

Residual components of said parts are typically withdrawn during the same or following separation sequences in the zone of one or more residual fractions or directed either to a recycle fraction or circulated in a circulation phase to be introduced back to the system to be finally withdrawn in the zone of one or more residual fractions. Betaine of said parts is typically directed to a sucrose recycle fraction to be added to dilute a feed solution and to increase the betaine content of the feed and to be withdrawn in a final betaine fraction.

The volume, introduction position and introduction step of said parts are determined on the basis of the retention volumes of the components of said parts, the volume of the resin bed through which components of the parts pass and the volume of the steps moving the components of said parts from the introduction position to the calculated target withdrawal position of the components during said same or following separation sequences while essentially maintaining the purity of the product fraction(s) and the yield of the product components.

It is essential that the volume, introduction position and introduction step of said parts are determined to be suitable so that the components of said parts at the withdrawal thereof either reach the region of the similar fast moving components of the feed or are retained to be eluted together with the faster moving components of the feed or allow the fast moving components of the separation profile to reach the slow moving components of said parts.

The volume, introduction position and introduction step of said parts are determined by first determining the target fraction or fractions and their volumes as well as the column(s) and step(s) in which the component(s) of said parts are to be withdrawn. For example, if the main component of said parts is betaine and/or sucrose, the betaine/sucrose component is to be withdrawn in some of the recycle fractions of another product component (e.g. betaine is withdrawn in a sucrose recycle fraction) which are withdrawn from predetermined columns in predetermined steps of the process. The sucrose recycle fraction may be e.g. a front slope part or a rear slope part of a sucrose subprofile. These recycle fractions are then recycled back to the feed for further separation and for further recovery of betaine/sucrose. If the main components of said parts are residual compounds, such as salts, the salt components are to be withdrawn in some of the zones of the residue fractions to be withdrawn from predetermined columns in predetermined steps of the process during the next or following sequences.

The retention volumes of the components of said parts for each separation system are experimentally determined for the resin beds in use. For example in the separation of molasses, the retention volume of betaine is approximately 70% (between 67% and 73%) of the resin bed volume used, and the retention volume of sucrose is approximately between 55% and 60% of the resin bed volume used for monovalent strong acid cation exchange resin beds (having a DVB content of 6 to 6.5%). The retention volume of the start of the conductivity peak (salts and large molecules) in the same molasses separation with the same resins is approximately between 28% and 34% of the resin bed volume, which is equal to the void volume of the resin bed. Also the peak broadening phenomenon must be taken into account when calculating the elution volumes, in which different components are eluted from the separation column.

The movement of different components (such as betaine, sucrose and salts) of said parts in the separation process, such as in a sequential SMB system, during one sequence and especially during the following 1 to 4 sequences can then be calculated on the basis of the retention volumes (Rt) of the components, the volume of the resin bed (BV) through which the components of the parts pass and the volume of the steps (V) moving the components of said parts during said sequences (calculated step by step). A component starts eluting from the separation system (column) when the volume of the steps moved through the system is equal to the retention volume of the component in question. This determines the target withdrawal position of the component concerned. When the target withdrawal position is known, the introduction volume, position and step of said parts as an eluent substituent can then be calculated upstream step by step so that the components of said parts end up and are withdrawn in the target fractions essentially during the following 1 to 4 sequences. This is achieved when the volume of the steps from the target withdrawal position to the introduction position of said parts is equal to the retention volume of the components of said parts through the resin bed from introduction to withdrawal. The volume of steps is calculated upstream from column to column step by step by summing up the volumes introduced to the columns in each step during the feeding, elution and circulation phases, starting with the target position.

The volumes of the parts as flow rates ($m^3/h$) may be measured either from the inlet or outlet of the columns.

The desired components are withdrawn during said same or following separation sequences. In one embodiment of the invention, the desired components are essentially withdrawn during the following 1 to 4 separation sequences.

The chromatographic separation system may be a batch system or an SMB system, which may be continuous or sequential.

In a preferred embodiment of the invention, the chromatographic separation system is a sequential SMB system described in U.S. Pat. No. 6,093,326, U.S. Pat. No. 5,127,957, U.S. Pat. No. 6,224,776 and U.S. Pat. No. 6,896,811.

The sequential chromatographic SMB system may contain one or more loops in the system. The system may also contain one or more separation profiles in a loop.

In one embodiment of the invention, the separation profile is circulated more than once or less than once through the resin bed of the system during one cycle.

The chromatographic separation resins in the partial packed beds of the separation system may be selected from those commonly used for the separation of betaine from betaine-containing solutions. Especially useful resins are strongly acid cation exchange resins (SAC) and weakly acid cation exchange resins (WAC), but even weakly basic anion exchange resins (WBA) and strongly basic anion exchange resins (SBA) can be used. The cation exchange resins (SAC and WAC) may be in monovalent or divalent form, such as in $H^+$, $Na^+$, $K^+$, $Ca^{2+}$, $Mg^{2+}$ or $Zn^{2+}$ form.

The resins may be styrenic or acrylic resins having a crosslinking degree in a range of 1 to 20%, for example 4 to 10% DVB (divinylbenzene). The crosslinking degree of the resins as a rule affects the retention volume of the resins. A typical mean particle size of the resins is 200 to 450 μm.

In one embodiment of the invention, said one or more parts are front slope parts or rear slope parts of a betaine subprofile, which may be very dilute but posses a high betaine content. This embodiment of the invention comprises introducing said front slope parts and/or rear slope parts of a betaine subprofile back to said separation system to replace a portion of the eluent water, followed by withdrawing betaine of said front slope or rear slope parts during the next sequence in a recycle fraction of a product component other than betaine, for example in a sucrose recycle fraction. The recycle fraction is recycled to the feed for further separation of betaine. Betaine from slopes is finally recovered in a betaine fraction, which has a higher dry solids concentration and may also have a higher betaine content than without circulation of the slopes.

Typically, the front and rear slope parts of a betaine subprofile have a dry solids concentration of 0.2% to 8% and a betaine content up to 80% on dry solids (DS).

Typically, the betaine yield to the sucrose recycle fraction by using circulated betaine front slope or rear slope parts as eluent replacement is more than 60%, preferably more than 80%, most preferably more than 85%.

The use of betaine front slope parts and/or rear slope parts as eluent replacement in the separation of beet molasses in a sequential SMB process typically provides a betaine fraction with a betaine purity of 40 to 90%, preferably 60 to 90% on DS, most preferable 80 to 90% on DS. A typical total betaine yield to the betaine fraction from the feed is in a range of 60 to 98%, preferably in the range of 85 to 98%. The dry solids concentration of the betaine fraction is increased by the method of the invention and is typically 2 to 6%.

In another embodiment of the invention, said one or more parts may be selected from front slope parts and rear slope parts of a residual subprofile. In this embodiment of the process of the invention, said front slope parts or rear slope parts of a residual subprofile are introduced back to said separation system to replace a portion of the eluent water, the components thereof are moved to the region of other residual components, followed by withdrawing the residual components of said slope parts in more than one residual fraction during the same or following 1 to 4 sequences.

In one embodiment of the invention, the front slope and/or rear slope of the residual subprofile may be divided into several subsections, which are introduced to the separation system as eluent replacement. It is also possible to circulate only some of the subsections as eluent replacement, while some of them are withdrawn from the system. Selection of a subsection for eluent replacement will be done according to its volume and its introduction (column and step) and withdrawal positions on the basis of the knowledge about its retention volume in the separation. Subsections for eluent replacement can be selected from the more dilute end, from the middle or from the most concentrated part of the residual fraction. The dry solids concentration of the subsections may vary from 0.5% to 15%.

In one embodiment of the separation of molasses, the front slope of the residual subprofile may be divided for example into four subsections (sections 1 to 4), whereby sections 1 and 3 are withdrawn from the separation system and sections 2 and 4 are used as eluent replacement by introducing them in calculated steps to different columns intermittently.

In a further embodiment of the invention, said one or more parts may be selected from front slope parts and rear slope parts of a sucrose subprofile. This embodiment of the invention comprises introducing said front slope parts or rear slope parts of a sucrose subprofile back to said separation system to replace a portion of the eluent water, followed by withdrawing sucrose of said front slope or rear slope parts during the next sequence in a recycle fraction. The recycle fraction is recycled to the feed for further separation of sucrose. Sucrose is finally recovered in a sucrose fraction.

In a still further embodiment of the invention, said one or more parts may comprise both (1) one or more parts of a betaine subprofile, such as front slope parts and/or rear slope parts of a betaine subprofile, and (2) one or more parts of the residual subprofile. Different parts may be combined or introduced separately to different eluent introduction positions to enable the withdrawal of the components of the parts in suitable fractions during the same or following sequences.

The volume of said parts is preferably less than that of the recycle fraction or residue fraction in which the components of said parts are to be withdrawn.

In one embodiment of the invention, said parts are introduced to the separation system as an intact separation profile as a continuous stream from another column.

In another embodiment of the invention, said parts are collected into a separate tank and introduced back to the separation system from the tank.

The total volume of said parts used for eluent replacement in the separation system is 1 to 50%, advantageously 5 to 20% of the volume of all steps moving the separation profile forward during one separation sequence.

Said parts are typically used to substitute 5 to 70%, preferably 10 to 30% of eluent water. The amount of replacement eluent is preferably the same as that of the omitted water eluent.

In a typical embodiment of the invention, the process provides a betaine product fraction with a betaine content of 40 to 96%, preferably 60 to 90% on DS.

The process provides a betaine yield of more than 60%, preferably more than 70%, more preferably more than 80%, most preferably more than 85% and especially more than 90% on the basis of the betaine in the betaine-containing feed solution.

In one embodiment of the invention, the process provides a sucrose product fraction with a sucrose content of 88 to 98% on DS and a sucrose yield in a range of 80 to 98% based on the sucrose in the sucrose-containing feed solution.

Said solution containing betaine is preferably a sugar beet derived solution, such as a molasses solution or a crystallization run-off or a solution thereof.

In a further embodiment of the invention, the invention relates to a method which has the following characteristic features:
said parts are selected from front slope parts and rear slope parts of a betaine subprofile and front slope parts and rear slope parts of a residual subprofile,
said parts are introduced back to the separation system to replace a portion of the eluent water,
betaine of said parts and/or the residual components of said parts are withdrawn during the next sequence in a sucrose recycle fraction, which is recycled to the feed, followed by
recovering betaine of said parts in a betaine product fraction and recovering the residual components of said parts in the residual fractions during the following separation sequences.

In this embodiment of the invention, said sucrose recycle fractions may be selected from front slope parts and rear slope parts of a sucrose subprofile.

In one embodiment of the separation of molasses, said front slope parts and rear slope parts of a betaine subprofile typically have a high betaine purity, but a low dry substance content. The introduction position and volume of said betaine-containing front slope parts and rear slope parts as an eluent substitute are calculated so that the betaine in said parts during the separation process moves to the sucrose recycle fraction. Said parts containing the slow-moving betaine are thus introduced into such a position that the residual components (salts) of the separation profile pass betaine of the parts and the new peak of the betaine from the parts will be within the collection interval of the sucrose recycle fraction. The recycle fraction is collected at a point where sucrose and residual components (salts) partly overlap. In this process, betaine can be efficiently recovered from the dilute betaine-containing front slope parts and rear slope parts of a betaine subprofile. Consequently, the concentration (dry substance and betaine) of the betaine product fraction rises and the water in the dilute betaine-containing front slope parts and rear slope parts is utilized as an eluent.

In another embodiment of the separation of molasses, parts of a residual subprofile are introduced back to the separation system so that the residual components (salts) are withdrawn in the last column of for example a 4-column separation system in a fraction where sucrose and betaine partly overlap and which is circulated in a loop to the first column. The salts and other fast-moving components pass betaine and/or sucrose in the separation profile and are finally withdrawn from the system in several withdrawal positions of the residual fractions during the following 1 to 4 sequences. Residual fractions can be withdrawn from the bottom of every column of the system.

Said solution containing betaine may also be a vinasse solution. Said vinasse may be derived from sugar beet or wheat. Consequently, circulations of parts described above relating to the separation of molasses can also be applied to the separation of vinasse.

In the process of the present invention, said one or more parts of the separation profile are typically utilized as eluent replacement within the same separation system. However, it is also possible to introduce said parts as eluent replacement to other similar parallel separation systems or to different separation systems.

The following examples illustrate the invention without limiting the invention in any way.

Example 1

2-Loop Chromatographic SMB Separation of Beet Molasses

Residual Containing PARTs

The process equipment included six columns connected in series, a feed pump, recycling pumps, an eluent water pump, heat exchangers, flow control means for out-coming liquids as well as inlet and product valves for the various process streams. The height of all columns was 4 m and the diameter was 5.15 m. The total resin volume of the SMB system was $6 \times 83.3 \, m^3 = 500 \, m^3$. Column 1 consists of two parts 1a and 1b, 2 meters each. The columns were packed with a strong acid gel type cation exchange resin (Dow resin) in $Na^+$ form. The divinylbenzene content of the resin was 6.5% and the mean bead size of the resin was 0.35 mm.

Before the separation, molasses was pre-coat filtered using diatomaceous earth as a filter aid. On-line dilution was used for thick molasses. The feed was composed as set forth below, whereby the percentages are given on a dry substance weight basis.

TABLE E1-1

| Composition of feed | |
|---|---|
| Sucrose, % on DS | 70.9 |
| Betaine, % on DS | 4.1 |
| Others, % on DS | 25 |

The fractionation was performed according to U.S. Pat. No. 6,093,326 by way of a 15-step SMB sequence as set forth below. The aim of the separation was to separate sucrose and betaine contained therein. The feed and the eluent were used at a temperature of 80° C. and ion exchanged water was used as an eluent.

Step 1: 1.5 $m^3$ of feed solution was pumped into the first column at a flow rate of 160 $m^3$/h, and a recycle fraction was collected from the last column (column 6).

Step 2: 5.0 $m^3$ of feed solution was pumped into the first column at a flow rate of 160 $m^3$/h, and a betaine fraction was collected from the fourth column. Simultaneously, 4.9 $m^3$ of eluent water was pumped into the fifth column at a flow rate of 161 $m^3$/h, and a recycle fraction was collected from the last column.

In steps 1 and 2, 5.1 $m^3$ of a portion of the residual fraction (PART 1) from column 1 was transferred to column 2 to act as an eluent replacer and to be removed from the system later during the following 1 to 3 sequences in the residual fraction from columns 1, 2 and 5. In a reference run, residual R1 was collected from the bottom of column 1.

Step 3: 3.0 $m^3$ of feed solution was pumped into the first column at a flow rate of 160 $m^3$/h, and a residual fraction (R4) was collected from the fourth column. Simultaneously, 3 $m^3$ of PART 1 was transferred from column 1 to column 2. Simultaneously, 3 $m^3$ of eluent water was pumped into the fifth column at a flow rate of 164 $m^3$/h, and a recycle fraction was collected from the last column.

Step 4: 5.6 $m^3$ of feed was pumped into the first column at a flow rate of 94 $m^3$/h, and a residual fraction (R1) was collected from the same column. Simultaneously, 10 $m^3$ of eluent water was pumped into the second column at a flow rate of 166 $m^3$/h, and a residual fraction (R4) was collected from the fourth column. Also simultaneously, 12.7 $m^3$ of eluent was pumped into the fifth column at a flow rate of 222 $m^3$/h, and a sucrose fraction was collected from the last column.

Step 5: 5.6 $m^3$ of feed was pumped into the first column at a flow rate of 91 $m^3$/h, and a residual fraction (R1) was collected from the same column. Simultaneously, 11.8 $m^3$ of eluent was pumped into the second column at a flow rate of 189 $m^3$/h and a sucrose fraction was collected from the last column.

Step 6: 8.8 $m^3$ of eluent was pumped into the first column at a flow rate of 140 $m^3$/h, and a sucrose fraction was collected from the last column.

Step 7: 13 $m^3$ was circulated in the column loop, formed with columns 1, 2 and 3, at a flow rate of 180 $m^3$/h. Simultaneously, 5.4 $m^3$ was circulated in the column loop, formed with columns 4, 5 and 6, at a flow rate of 72 $m^3$/h.

Step 8: 8.4 $m^3$ was circulated in the column loop, formed with columns 1, 2 and 3, at a flow rate of 180 $m^3$/h. Simultaneously, 4 $m^3$ of eluent water was pumped into the last column (column 6) at a flow rate of 85 $m^3$/h, and a betaine fraction was collected from the fifth column.

In step 8, 4.2 $m^3$ of a portion of the residual fraction (PART 2) from column 2 was transferred to column 3 to act as an eluent replacer and to be removed from the system later during the following 1 to 3 sequences in the residual fraction from columns 4 and 6.

Step 9: 5.5 $m^3$ of eluent water was pumped into the third column at a flow rate of 175 $m^3$/h, and a residual fraction (R2) was collected from the second column. Simultaneously, 5.1 $m^3$ of eluent was pumped into the last column at a flow rate of 180 $m^3$/h, and a residual fraction was collected from the fifth column.

Step 10: 8.3 $m^3$ of eluent water was pumped into the first column at a flow rate of 167 $m^3$/h, and a residual fraction (R2) was collected from the second column. Simultaneously, 7.0 $m^3$ of eluent was pumped into the third column at a flow rate of 140 $m^3$/h and a betaine fraction was collected from the same column. Also simultaneously, 8.1 $m^3$ of eluent was pumped into the last column at a flow rate of 163 $m^3$/h, and a residual fraction (R5) was collected from the fifth column.

Step 11: 19.5 $m^3$ of eluent water was pumped into the first column at a flow rate of 172 $m^3$/h, and a betaine fraction was collected from the second column. Simultaneously, 20.0 $m^3$ was circulated in the column loop, formed with columns 4, 5 and 6, at a flow rate of 181 $m^3$/h.

Step 12: 7.5 m³ was circulated in the column loop, formed with columns 1b, 2 and 3, at a flow rate of 186 m³/h. Simultaneously, 7.0 m³ was circulated in the column loop, formed with columns 4, 5 and 6, at a flow rate of 172 m³/h.

In step 12, 3 m³ of a portion of the residual fraction (PART 3) from column 3 was transferred to column 1/lower part (column 1b) to act as an eluent replacer and to be removed from the system later during the next 1 to 3 sequences.

Step 13: 2.0 m³ was circulated in the column loop, formed with columns 1b, 2 and 3, at a flow rate of 186 m³/h. Simultaneously, 2.0 m³ of eluent water was pumped into the fourth column at a flow rate of 140 m³/h, and a betaine fraction was collected from the sixth column.

Step 14: 14.5 m³ of eluent water was pumped into the fourth column at a flow rate of 140 m³/h, and a residual fraction (R3) was collected from the third column.

In step 14, 14.5 m³ of a portion of the residual fraction (PART 6) from column 6 was transferred to column 1b to act as an eluent replacer and to be removed from the system later during the following 1 to 3 sequences in the residual fractions from columns 2 and 5 in steps 9 and 10 and in the recycle fraction in step 2.

Step 15: 21.6 m³ was circulated in the column loop, formed with columns 1, 2 and 3, at a flow rate of 178 m³/h. Simultaneously, 24.5 m³ was circulated in the column loop, formed with columns 4, 5 and 6, at a flow rate of 200 m³/h.

After equilibration of the system, the following fractions were drawn from the system: a residual fraction from columns 1, 2, 3, 4 and 5, recycle fractions from the last column, sucrose product fractions from the last column, and betaine product fractions from columns 3, 4, 5, and 6. The recycle fractions were used for the dilution of molasses to the feeding concentration. The results including HPLC analyses for the combined fractions are set forth in Table E1-2 below. In the test run, 5.1 m³ of PART 1, a portion of the residual fraction from column 1 was introduced to the second column in steps 2 and 3. From column 2, 4.2 m³ of PART 2, a portion of the residual fraction from column 2 was introduced to the third column in step 8. From column 3, 3 m³ of PART 3, a portion of the residual fraction from column 3 was introduced to the second half of column 1 in steps 12 and 13. From column 6, 14.5 m³ of PART 6, a portion of the residual fraction from column 6 was introduced to the first column in step 14. The W/F (water to feed, vol/vol) ratio was reduced from 4.5 to 4.0.

TABLE E1-2

| | Combined residual | Combined recycle | Combined sucrose | Combined betaine |
|---|---|---|---|---|
| Volume, m³ | 65.6 | 9.4 | 33.3 | 37.5 |
| Dry solids, weight-% | 6.1 | 17.0 | 28.9 | 2.9 |
| Sucrose % on DS | 20.7 | 73.0 | 92.2 | 4.18 |
| Betaine, % on DS | 1.2 | 0 | 0 | 61 |
| Others, % on DS | 78.4 | 26.6 | 7.8 | 34.82 |

The overall yield calculated from these fractions was 91.1% for sucrose and 92.2% for betaine. In the reference run, all residual was taken out from the system and the W/F (eluent water to feed, vol/vol) ratio was 4.5.

These new steps create an internal loop for the recycled dry substance where a balance was achieved after several sequences raising the dry substance of the residual fractions without decreasing the yield or purity of sucrose or betaine fractions.

Calculation of the column and the step into which the compounds of various PARTS ended up was done assuming that the front of PART compounds (=residual compounds) has a retention volume of 31.2% BV. Also band broadening was taken into account empirically. The movement of PART compounds in the SMB system was calculated by subtracting the volume introduced to a column from the column void step by step from column to column, starting with a step where water as an eluent was replaced by the eluent replacement solution (PART). This method is very accurate for the profile front movement of the residual compounds. Tailing of the profile was an estimate and it was proved by this example that some tailing is evident but it did not deteriorate sucrose and betaine fractions.

Example 2

2-Profile Chromatographic SMB Separation of Beet Molasses

Residual Containing PARTS

The process equipment included four columns connected in series, a feed pump, recycling pumps, an eluent water pump, heat exchangers, flow control means for out-coming liquids as well as inlet and product valves for the various process streams. The height of all columns was 5.5 m and the diameter was 5.1 m. The volume of the total resin bed was 4×110 m³=440 m³. All columns consist of two parts, the height of each being 2.75 meters. The columns were packed with a strong acid gel type cation exchange resin (part of the resin manufactured by Bayer and part by Finex Oy) In Na⁺ form. The divinylbenzene content of the resin was 6.5% and the mean bead size of the resin was 0.35 mm.

Before the separation, molasses was pre-coat filtered using diatomaceous earth as a filter aid. On-line dilution was used for thick molasses. The feed was composed as set forth below, whereby the percentages are given on a dry substance weight basis.

TABLE E2-1

| Composition of feed | |
|---|---|
| Sucrose, % on DS | 62.3 |
| Betaine, % on DS | 5.7 |
| Others, % on DS | 32 |

The fractionation was performed according to U.S. Pat. No. 6,224,776 by way of a 16-step SMB sequence as set forth below. The aim of the separation was to separate and recover sucrose and betaine contained therein. The feed and the eluent were used at a temperature of 80° C. and ion exchanged water was used as an eluent. A portion of the eluent water was replaced in several steps in various phases during a sequence with a part of a residual fraction from several steps and called PART X (taken out from column X). PARTS contained mainly ionic components, e.g. inorganic salts, organic acids and amino acids, and were referred to as "others" in the tables.

Step 1: 10 m³ of feed solution was pumped into the first column at a flow rate of 70 m³/h, and a recycle fraction was collected from the last column (column 4).

Step 2: 4.8 m³ of feed solution was pumped into the first column at a flow rate of 75 m³/h, and a residual fraction (R1) was collected from the same column. A portion of components of PART 4 will be removed in R1. Simultaneously, 3.5 m³ of eluent water was pumped into the second column at a flow rate of 50 m³/h, and a sucrose fraction was collected from the last column.

A portion of PART 4 transferred to column 1 in step 7 two sequences earlier was withdrawn in step 2 as a residual fraction (R1) from column 1. The rest of PART 4 was withdrawn in the following residual fractions (R2, R3 and R4) in the following steps.

Step 3: 9.2 m$^3$ of feed solution was pumped into the first column at a flow rate of 60 m$^3$/h, and a residual fraction (R1) was collected from the same column. Simultaneously, 13.5 m$^3$ of water eluent was pumped into the second column at a flow rate of 75 m$^3$/h, and a residual fraction (R3) was collected from the third column. Components of PART 2 will be removed in R3. Also simultaneously, 22.5 m$^3$ of water eluent was pumped into the last column at a flow rate of 120 m$^3$/h, and a sucrose fraction was collected from the same column.

R3 contains 7.8 m$^3$ of PART 2 and will be withdrawn in step 3 two sequences later than introduced in steps 9 and 12 to column 3.

Step 4: 9.8 m$^3$ of water eluent was pumped into the fourth column at a flow rate of 95 m$^3$/h, and a residual fraction (R1) was collected from the first column. Simultaneously, 8.4 m$^3$ of water eluent was pumped into the second column at a flow rate of 85 m$^3$/h, and a residual fraction (R3) was collected from the third column.

Step 5: 9.0 m$^3$ was circulated in the column loop, formed with all columns, at a flow rate of 110 m$^3$/h.

PART 2-1 and PART 2-2 in column 1 were broadened to be one PART 2 in step 5 in the following sequence after the introduction of PART 2-1 in step 9 and PART 2-2 in step 12.

Step 6: 29 m$^3$ of eluent water was pumped into the first column at a flow rate of 115 m$^3$/h, and a betaine fraction was collected from the fourth column.

Step 7: 8 m$^3$ of eluent water was pumped into the third column at a flow rate of 110 m$^3$/h, and a residual fraction (R2) was collected from the second column. Simultaneously, 8 m$^3$ of PART 4 (a portion of R 4) was transferred from column 4 to column 1 as a PART to replace eluent water.

Step 8: 4.7 m$^3$ of eluent water was pumped into the third column at a flow rate of 100 m$^3$/h, and a residual fraction (R4) was collected from the fourth column. Columns 1 and 2 wait for the next step.

Step 9: 3 m$^3$ of eluent water was pumped into the first column at a flow rate of 100 m$^3$/h, and a residual fraction (R4) was collected from the fourth column and all columns were connected to each other in series. Simultaneously, 3 m$^3$ of PART 2-1 (a portion of R2) was transferred to column 3 as an eluent replacer.

Step 10: 9.5 m$^3$ of eluent water was pumped into the first column at a flow rate of 105 m$^3$/h, and a residual fraction (R2) was collected from the second column. Simultaneously, 8.3 m$^3$ was pumped into the third column at a flow rate of 75 m$^3$/h, and a residual fraction was collected from the fourth column.

Step 11: 1.2 m$^3$ of eluent water was pumped into the third column at a flow rate of 110 m$^3$/h, and a residual fraction (R2) was collected from the second column.

Step 12: 27.5 m$^3$ was circulated in the column loop, formed with all columns, at a flow rate of 120 m$^3$/h. Simultaneously, 3 m$^3$ of PART 2-2 (a portion of R2) was transferred from column 2 to column 3 as an eluent replacer.

Figure 1:
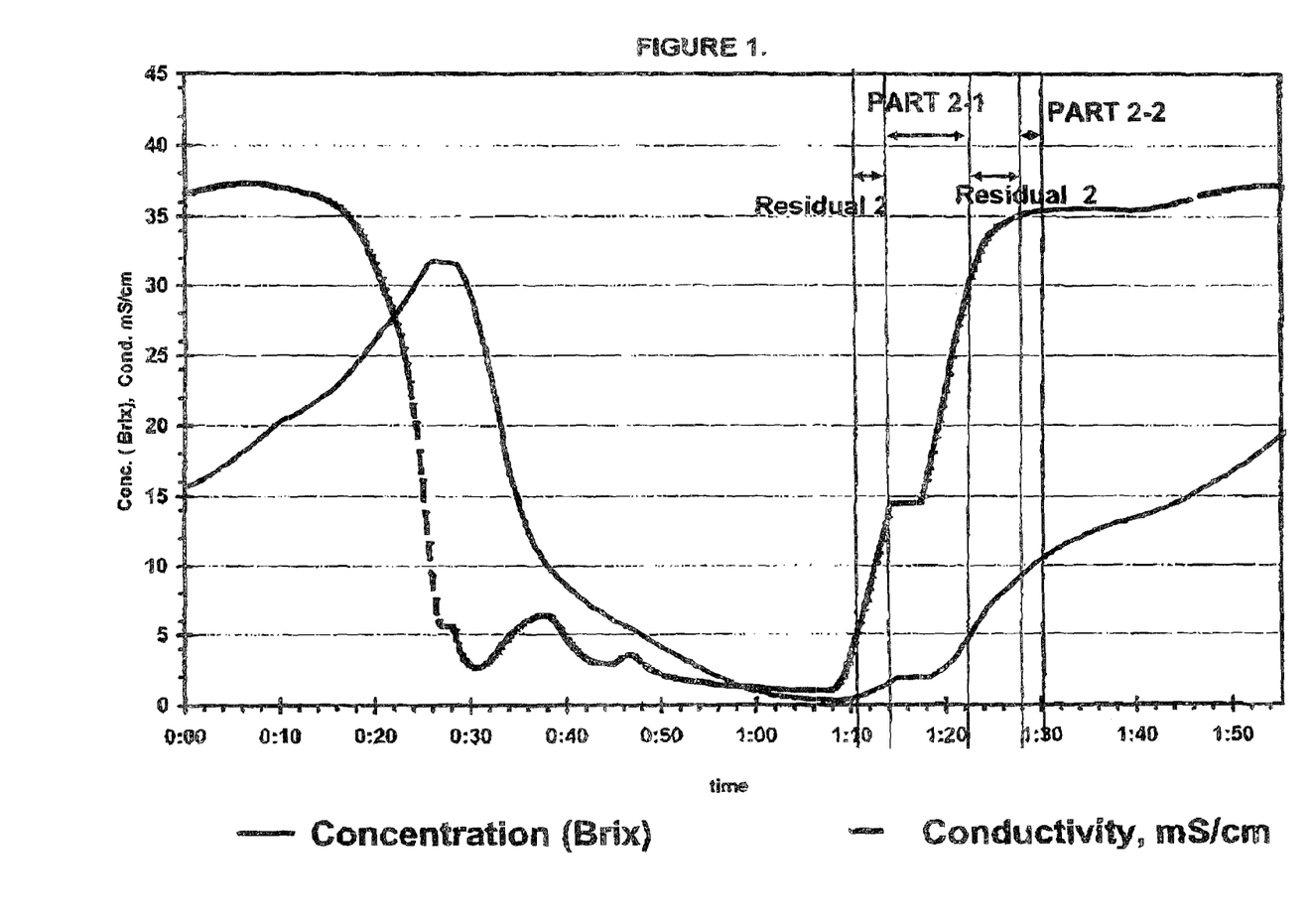
FIG. 1 shows the separation profile and outflow fractions from column 2.
Figure 2:
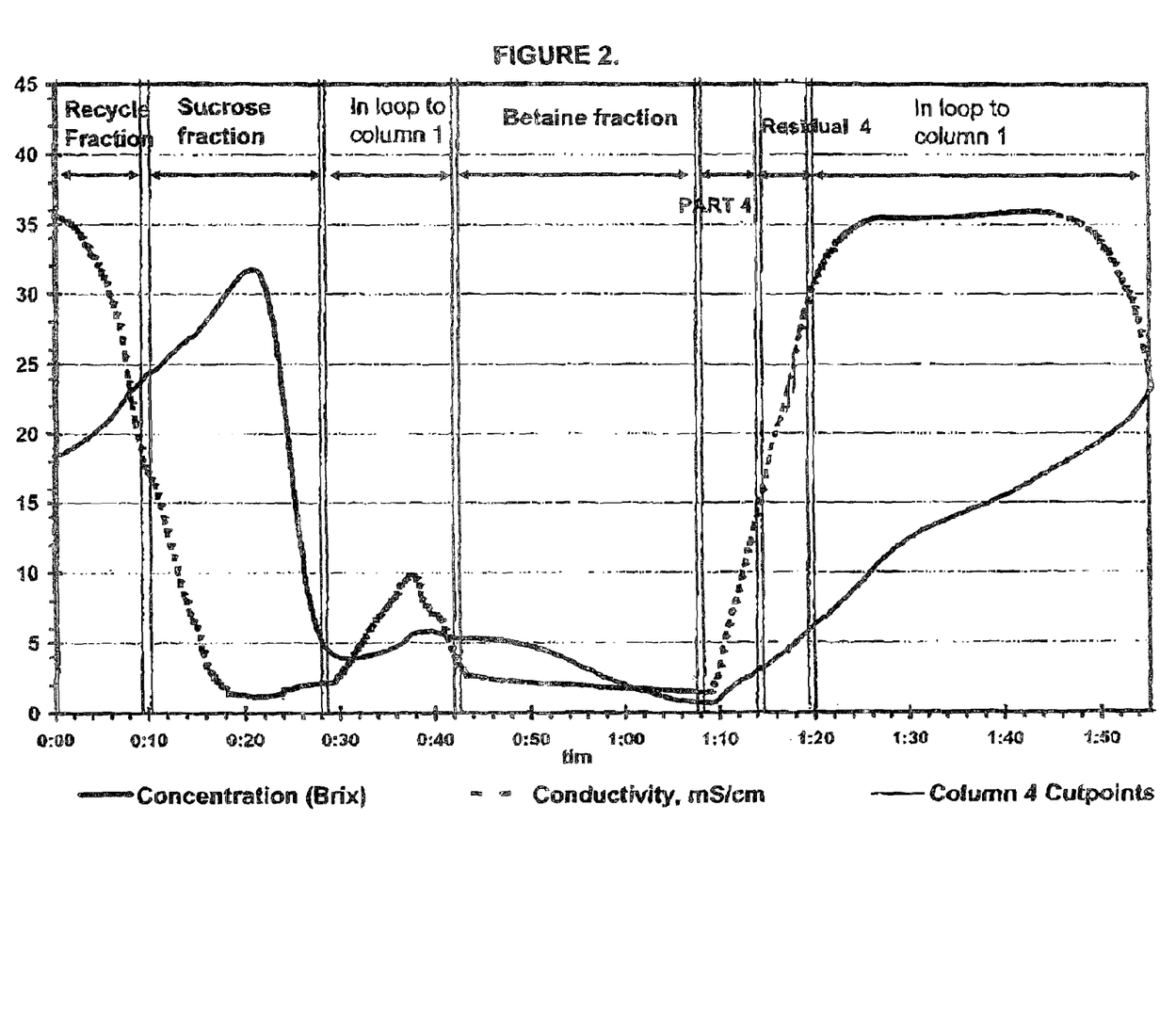
FIG. 2 shows the separation profile and outflow fractions from column 4.

After equilibration of the system, the following fractions were drawn from the system: a residual fraction from columns 1 (R1), 2 (R2), 3(R3), 4(R4), recycle fractions of the sucrose front from the last column, sucrose product fractions from the last column, and betaine product fractions from the last column. The recycle fraction of the sucrose front was used for dilution of molasses to adjust the concentration of the feed. The results, including HPLC analyses for the combined fractions, are set forth in Table E2-2 below. In the test run, 8 m$^3$ of PART 4 from column 4 was introduced to the first column in step 7, and 6 m$^3$ of PART 2 (PART 2-1 and PART 2-2) from the second column was introduced to the third column in steps 9 and 12. The W/F (water eluent to feed, vol/vol) ratio was reduced from 6.0 to 5.1. The separation profile and outflow fractions from columns 2 and 4 are shown in FIGS. 1 and 2.

TABLE E2-2

|  | Combined residual | Combined recycle | Combined sucrose | Combined Betaine |
|---|---|---|---|---|
| Volume, m$^3$ | 80.4 | 10 | 26 | 29 |
| Dry solids, weight-% | 6.3 | 18.4 | 24.5 | 3.9 |
| Sucrose % on DS | 13 | 80.5 | 91.0 | 1.96 |
| Betaine, % on DS | 0.5 | 0 | 0 | 75.0 |
| Others, % on DS | 86.5 | 19.5 | 9 | 23.04 |

The overall yield calculated from these fractions was 90.5% for sucrose and 97.1% for betaine. In the reference run, all residual was taken out from the system and the W/F (eluent water to feed, vol/vol) ratio was 6.0. By using circulations of PARTS, the amount of water eluent was reduced by 15% compared to the reference.

These new steps create an internal loop for the recycled dry substance where a balance was achieved after several sequences raising the dry substance of residual fractions without decreasing the yield or purity of sucrose or betaine fractions.

Calculation of the position (column) and the step where the compounds of various PARTS (=portions of the residual fraction) ended up was done assuming that the front of PART compounds (=residual compounds) have a void of 34.5% BV. Also band broadening was taken into account empirically. The movement of PART compounds in the SMB system was calculated by subtracting the volume introduced to a column from the column void step by step from column to column starting with a step where the water eluent was replaced by PART solution. This method is very accurate for the profile front movement of the residual compounds. Tailing of the profile was an estimate and it was proved by this example that some tailing is evident but it did not deteriorate sucrose and betaine fractions.

Example 3

Chromatographic SMB Separation of Beet Molasses

Betaine Containing PARTS

The process equipment included three columns connected in series, a feed pump, recycling pumps, an eluent water pump, heat exchangers, flow control means for out-coming liquids as well as inlet and product valves for the various process streams. The equipment included also an eluent replacement tank, pump, lines, flow control means and valves for the fractions to be used as eluent water replacement. The height of all columns was 5.0 m and the diameter was 0.111 m. The total resin volume of the system was 3×48.4 l=145.2 liters. The columns were packed with a strong acid gel type cation exchange resin (manufactured by Finex) in Na$^+$ form. The divinylbenzene content of the resin was 5.5% and the mean bead size of the resin was 0.33 mm.

Before the separation, beet molasses was diluted with ion exchanged water to 60 weight-%, and 1.5% sodium carbonate on DS was added. The solution was then pH adjusted with NaOH to a pH of about pH 9.7, heated to 60° C. and cooled down to 40° C. during 15 hours of mixing. Thereafter, the beet molasses was pre-coat filtered by using diatomaceous earth as a filter aid. The pre-coat amount was 1 kg/m², the body feed amount was 0.5% on DS, and the temperature was 60° C. Final pH adjustment was done with HCl to pH 8.6.

For the separation tests, the beet molasses was still evaporated to 78 weight-% and filtered through a 5 μm bag filter. During the tests, the feed dry substance was adjusted by mixing 78 weight-% beet molasses with a collected recycle fraction in a separate tank before feeding it to the column. The feed was composed as set forth below, whereby the percentages are given on a dry substance weight basis.

TABLE E3-1

| Composition of feed | |
|---|---|
| Dry solids, weight-% | 45.7 |
| Sucrose, % on DS | 60.1 |
| Betaine, % on DS | 4.0 |
| Others, % on DS | 35.9 |

The fractionation was performed by way of a sequential simulated moving bed (SMB) system by using a special process mode described in U.S. Pat. No. 6,896,811 by circulating the formed separation profile twice through the resin bed of the SMB system and using a 17-step SMB sequence as set forth below. The aim of the separation was to separate sucrose and betaine contained therein. The feed and the eluent were used at a temperature of 80° C. and ion exchanged water was used as the eluent water.

Step 1: 2.8 l of feed solution was pumped into the first column at a flow rate of 50 l/h, and a sucrose recycle fraction was collected from the last column (column 3).

Step 2: 10.4 l of feed solution was pumped into the first column at a flow rate of 38 l/h, and a residual fraction (R1) was collected from the same column. Simultaneously, 8.7 l of eluent water was pumped into the second column at a flow rate of 79 l/h, and a recycle fraction was collected from the last column (column 3).

Step 3: The collection of the residual fraction (R1) from the first column was continued. Simultaneously, 11.0 l of eluent water was pumped into the second column at a flow rate of 79 l/h, and a sucrose fraction was collected from the last column (column 3).

Step 4: 6.0 l of feed solution was pumped into the first column at a flow rate of 55 l/h, and a sucrose fraction was collected from the last column.

Step 5: 7.6 l was circulated in the column loop, formed with all columns, at a flow rate of 60 l/h.

Step 6: 4.9 l of eluent water was pumped into the third column at a flow rate of 60 l/h, and a residual fraction (R2) was collected from the second column.

Step 7: 16.8 l of eluent water was pumped into the third column at a flow rate of 70 l/h, and first, 2.0 l of a betaine-containing PART (B1), then 10.8 l of betaine fraction, and finally 4.0 l of a betaine-containing PART (B2) were collected from the last column. PART fractions B1 and B2 were collected into the same tank and used as an eluent replacement later in step 10.

Step 8: 17.3 l was circulated in the column loop, formed with all columns, at a flow rate of 60 l/h. The circulation was continued 4 liters more than in the reference test, to use a portion of the residual fraction from column 3 as a PART (R) as a replacer of the eluent water. The movement of the front of the PART (R) components (salts, organic acids, etc.) is calculated by using a retention volume of 30% BV.

Step 9: 10.6 l of eluent water was pumped into the first column at a flow rate of 60 l/h, and a residual fraction (R3) was collected from the third column.

Step 10: 6.0 l of the betaine-containing PART (B1 and B2) from the tank was pumped into the first column as the eluent water replacement at a flow rate of 60 l/h, and the collection of a residual fraction from the third column was continued.

Calculation: The target was to withdraw, later in the next sequence, compounds of PART (B1+B2) from column 3 in steps 1 and 2 in sucrose recycle fractions to be used for dilution of molasses feed.

The retention volume of betaine was 66% of the bed volume (BV). Betaine of PART (B1+B2) in step 10 started eluting out from the bottom of column 3, when 96 liters (=0.66× 145.21 l) was used to move betaine of PART (B1+B2) forward in the columns. The target volume was reached in the next sequence in steps 1 and 2 during the collection of the sucrose recycle fractions.

Step 11: 16.8 l was circulated in the column loop, formed with all columns, at a flow rate of 70 l/h.

Step 12: The loop was opened and 7.6 l of eluent water was pumped into the second column at a flow rate of 65 l/h, and a residual fraction (R1) was collected from the first column.

Step 13: 13.3 l was circulated in the column loop, formed with all columns, at a flow rate of 60 l/h.

Step 14: 12.5 l of eluent water was pumped into the third column at a flow rate of 60 l/h, and a residual fraction (R2) was collected from the second column.

Step 15: 13.2 l was circulated in the column loop, formed with all columns, at a flow rate of 65 l/h.

Step 16: 15.0 l of eluent water was pumped into the first column at a flow rate of 65 l/h, and a residual fraction (R3) was collected from the third column.

Step 17: 10.7 l was circulated in the column loop, formed with all columns, at a flow rate of 65 l/h.

After equilibration of the system, the following fractions were drawn from the system: two residual fractions from all columns, betaine-containing PART fractions B1 and 82 to be used as an eluent replacement from the third column, recycle fractions from the third column, sucrose product fractions from the third column and a betaine product fraction from the third column.

The results, including HPLC analyses for the combined residual, recycle, sucrose, betaine and PART fractions, are set forth in the table below.

TABLE E3-2

| | Combined residual | Combined recycle | Combined sucrose | Combined betaine | Combined PART (B1 + B2) |
|---|---|---|---|---|---|
| Volume, l | 67.0 | 11.5 | 17.0 | 10.8 | 6.0 |
| Dry solids, weight-% | 3.6 | 17.2 | 29.3 | 3.5 | 1.8 |
| Dry solids, g/100 ml | 3.7 | 18.3 | 32.9 | 3.6 | 1.8 |
| Sucrose % on DS | 5.9 | 53.4 | 93.4 | 0.7 | 17.5 |
| Betaine, % on DS | 1.3 | 3.3 | 0.1 | 81.2 | 76.4 |
| Others, % on DS | 92.8 | 43.3 | 6.5 | 18.1 | 6.1 |

The overall yield calculated from these fractions was 97.2% for sucrose and 89.3% for betaine. The water/feed (vol/vol) W/F ratio for the separation was 4.5. In the experiment, the betaine content in the betaine fraction was increased by circulating betaine from the betaine containing PART fractions (B1+B2) to the sucrose recycle fraction and back to the feed solution. The concentration of the combined residual fraction was increased by circulating a first part of the residuals within the separation system in steps 8 and 11. In a reference run without circulation of betaine and residual containing PART fractions, the betaine yield was 73.1%, and the betaine content was 79.5% on DS in the betaine fraction, the volume of combined residual fractions was 73.7 liters, and the separation W/F (vol/vol) ratio was 4.9. The reduction of fresh eluent water used in the experiment was 9% compared to the reference run.

Example 4

Chromatographic SMB Separation of Beet Molasses

Betaine-Containing PARTS

The process equipments, SMB columns, resins and pretreatments of beet molasses were similar to those in Example 3. The feed in the test was composed as set forth below, whereby the percentages are given on a dry substance weight basis.

TABLE E4-1

| Composition of feed | |
|---|---|
| Dry solids, weight-% | 45.6 |
| Sucrose, % on DS | 60.3 |
| Betaine, % on DS | 4.0 |
| Others, % on DS | 35.7 |

The fractionation was performed by way of a sequential simulated moving bed (SMB) system by using a special process mode described in U.S. Pat. No. 6,896,811 by circulating the formed separation profile twice through the resin bed of the SMB system and using of a 16-step SMB sequence as set forth below. The aim of the separation was to separate sucrose and betaine contained therein. The feed and the eluent were used at a temperature of 80° C. and ion exchanged water was used as an eluent.

Step 1: 2.8 l of feed solution was pumped into the first column at a flow rate of 50 l/h, and a sucrose recycle fraction was collected from the last column (column 3).

Step 2: 10.4 l of feed solution was pumped into the first column at a flow rate of 33 l/h, and first, 4.0 l of a betaine-containing PART (B1+R1) and then 6.4 l of a residual fraction were collected from the same column. Simultaneously, 19.4 l of eluent water was pumped into the second column at a flow rate of 79 l/h, and first, 8.7 l of a recycle fraction and then 10.7 l of sucrose recycle fraction were collected from the last column.

Step 3: 6.0 l of feed solution was pumped into the first column at a flow rate of 55 l/h, and a sucrose fraction was collected from the last column.

Step 4: 7.6 l was circulated in the column loop, formed with all columns, at a flow rate of 60 l/h.

Step 5: 4.5 l of eluent water was pumped into the third column at a flow rate of 60 l/h, and a residual fraction was collected from the second column.

Step 6: 14.8 l of eluent water was pumped into the third column at a flow rate of 70 l/h, and first, 2.0 l of a betaine-containing PART (B2), then 10.8 l of betaine fraction, and finally 2.0 l of a betaine-containing PART (B3) were collected from the last column. PART fractions were collected into a separate tank and used as an eluent replacement.

Step 7: 17.3 l was circulated in the column loop, formed with all columns, at a flow rate of 65 l/h. The circulation was continued 4 liters more than in the reference test to use a portion of the residual fraction from column 3 as a PART (R3) in a dilute concentration as a replacer for the water eluent. The movement of the front of the PART (R3) components (salts, organic acids etc.) is calculated by using a retention volume of 30% BV.

Step 8: 7.5 l of eluent water was pumped into the first column at a flow rate of 65 l/h, and a residual fraction was collected from the third column.

Step 9: 11.0 l of PART containing betaine and residual components (B1+R1, B2, B3, B4+R3) was pumped into the first column as an eluent water replacement at a flow rate of 60 l/h, and the residual fraction collection from the third column was continued. The calculation of the movement of components in PARTS was done in a manner similar to that in the previous examples.

Step 10: 16.8 l was circulated in the column loop, formed with all columns, at a flow rate of 70 l/h.

Step 11: 4.1 l of eluent water was pumped into the second column at a flow rate of 65 l/h, and a residual fraction was collected from the first column.

Step 12: 13.3 l was circulated in the column loop, formed with all columns, at a flow rate of 60 l/h.

Step 13: 15.0 l of eluent water was pumped into the third column at a flow rate of 60 l/h, and a residual fraction was collected from the second column.

Step 14: 13.2 l was circulated in the column loop, formed with all columns, at a flow rate of 70 l/h.

Step 15: 15.0 l of eluent water was pumped into the first column at a flow rate of 65 l/h, and first, 3.0 l of a betaine-containing PART (B4+R3) and then 12.0 l of a residual fraction were collected from the third column. PART (B4+R3) fraction was collected into the separate tank and used as an eluent replacement in step 9.

Step 16: 10.7 l was circulated in the column loop, formed with all columns, at a flow rate of 65 l/h.

After equilibration of the system, the following fractions were drawn from the system: two residual fractions from all columns, betaine-containing PART fractions used as eluent replacement from the first and last columns, recycle fractions from the last column, sucrose product fractions from the last column, and a betaine product fraction from the last column.

The results, including HPLC analyses for the combined residual, recycle, sucrose, betaine and PART fractions, are set forth in the table below.

TABLE E4-2

| | Combined residual | Combined recycle | Combined sucrose | Combined Betaine | Combined PART |
|---|---|---|---|---|---|
| Volume, l | 60.5 | 11.5 | 16.7 | 10.8 | 11.0 |
| Dry solids, weight-% | 4.7 | 17.2 | 29.1 | 3.4 | 1.8 |
| Dry solids, g/100 ml | 4.8 | 18.3 | 32.6 | 3.4 | 1.8 |
| Sucrose % on DS | 5.5 | 55.5 | 94.6 | 1.0 | 2.3 |
| Betaine, % on DS | 1.2 | 3.3 | 0.1 | 82.0 | 49.7 |
| Others, % on DS | 93.3 | 41.2 | 5.3 | 17.0 | 48.0 |

The overall yield calculated from these fractions is 96.9% for sucrose and 88.4% for betaine. The W/F ratio (vol/vol) for the separation was 4.2. In the experiment, the concentration and betaine content of the betaine fraction was increased by circulating betaine from the betaine-containing PART fractions (as four different PARTS) to the recycle fraction and back to the feed solution. In the experiment, the concentration of the residual fraction was increased by circulating residual components from the PART fractions to the residual fractions. The residual fraction was further concentrated by circulating a first part of the residual components inside the separation system in steps 7 and 10. In a reference separation process without taking and recycling PART fractions containing betaine and residual, the betaine yield in the betaine fraction was only 73.1% and the betaine content was 79.5% on DS, the combined residual volume was 73.7 liters and the separation W/F ratio was 4.9.

The amount of eluent water by using circulations of PARTS was reduced by 18% compared with the reference run.

On an industrial scale, the separate intermediary tank for PARTS may serve several SMB systems operating with the same feed molasses. It is also possible to use PART fractions collected from different separations as long as the components present in the PART fractions can be withdrawn in desired product or residual fractions. For example betaine-containing residual fractions from other betaine molasses separations may be used here as a PART fraction.

It will be obvious to a person skilled in the art that, as technology advances, the inventive concept can be implemented in various ways. The invention and its embodiments are not limited to the examples described above but may vary within the scope of the claims.

The invention claimed is:

1. A process for fractionating a betaine-containing solution in a chromatographic separation system, which comprises one or more columns containing one or more partial packed beds, comprising
feeding the betaine-containing solution into the separation system,
introducing an eluent into the separation system to elute components of the betaine-containing solution to form a separation profile, and
recovering a betaine product fraction, one or more residual fractions, and optionally one or more recycle fractions, and one or more other product fractions, and further comprising
introducing one or more parts of the separation profile to one or more eluent introduction positions of the separation system in one or more part feeding phases to substitute a portion of the eluent, said parts comprising one or more components selected from betaine, one or more other product components, and one or more residual components,
moving said parts with their components forward in the separation system by using a sequence of steps, which steps comprise one or more of a feeding phase, a circulation phase, and an elution phase, and
withdrawing components of said parts during the same or following separation sequences in one or more residual fractions and/or in one or more recycle fractions and/or in one or more product fractions,
whereby the volume, introduction position and introduction step of said parts are determined on the basis of the retention volumes of the components of said parts, the volume of the resin bed through which the components of the parts pass and the volume of the steps moving the components of the parts from the introduction position to the calculated target withdrawal position of the components during said same or following separation sequences while essentially maintaining or improving the purity of the product fraction(s) and the yield of the product components.

2. A process as claimed in claim 1, wherein the components of said parts are essentially withdrawn during the following 1 to 4 separation sequences.

3. A process as claimed in claim 1, wherein the chromatographic separation system is a batch system.

4. A process as claimed in claim 1, wherein the chromatographic separation system is a sequential simulated moving bed (SMB) system.

5. A process as claimed in claim 4, wherein the sequential chromatographic SMB system contains one or more loops in the system.

6. A process as claimed in claim 4, wherein the sequential chromatographic SMB system contains one or more separation profiles in a loop.

7. A process as claimed in claim 4, wherein the separation profile is circulated more than once or less than once through the resin bed of the system during one cycle.

8. A process as claimed in claim 1, wherein said one or more parts contain components selected from betaine, sucrose, salts, organic acids and salts thereof, amino acids, and glycerol.

9. A process as claimed in claim 1, wherein said one or more parts are front slope parts or rear slope parts of a betaine subprofile.

10. A process as claimed in claim 9, wherein the betaine content of the front slope parts and/or rear slope parts of a betaine subprofile is up to 80% on DS.

11. A process as claimed in claim 9, wherein the dry solids concentration of the front slope parts and/or rear slope parts of a betaine subprofile is 0.2% to 8%.

12. A process as claimed in claim 1, wherein said front slope parts and/or rear slope parts of a betaine subprofile are introduced back to said separation system to replace a portion of the eluent water, and during the next sequence, betaine of said front slope and/or rear slope parts is withdrawn in a sucrose recycle fraction to be recycled to the feed and to be recovered in a betaine fraction.

13. A process as claimed in claim 12, wherein the betaine yield to the sucrose recycle fraction from the circulated betaine front slope and/or rear slope parts is more than 60%, preferably more than 80%, and most preferably more than 85%.

14. A process as claimed in claim 1, wherein said one or more parts are front slope parts or rear slope parts of a residual subprofile.

15. A process as claimed in claim 14, wherein the dry solids concentration of the front slope parts of a residual subprofile is 0.5% to 10%.

16. A process as claimed in claim 14, wherein said front slope parts or rear slope parts of a residual subprofile are introduced back to said separation system to replace a portion of the eluent water, and residual components of said front slope parts or rear slope parts are withdrawn in more than one residual fraction during the same or following 1 to 4 sequences.

17. A process as claimed in claim 1, wherein said one or more parts are front slope parts or rear slope parts of a sucrose subprofile.

18. A process as claimed in claim 1, wherein the volume of said parts is 1 to 50% of the volume of all steps moving the separation profile forward during one separation sequence.

19. A process as claimed in claim 1, wherein the volume of said parts is preferably less than that of the recycle fraction or residue fraction in which the components of said parts are to be withdrawn.

20. A process as claimed in claim 1, wherein said parts are introduced to the separation system as an intact separation profile.

21. A process as claimed in claim 1, wherein said parts are collected into a separate tank and introduced to the separation system from the tank.

22. A process as claimed in claim 1, wherein said parts are selected from front slope parts and rear slope parts of a betaine subprofile and front slope parts and rear slope parts of a residual subprofile, said parts are introduced back to the separation system to replace a portion of the eluent water, betaine of said parts and/or the residual components of said parts are withdrawn during the next sequence in a sucrose recycle fraction which is recycled to the feed, followed by recovering betaine of said parts in a betaine product fraction and/or recovering the residual components of said parts in the residual fractions during the following separation sequences.

23. A process as claimed in claim 22, wherein said sucrose recycle fractions are selected from front slope parts and rear slope parts of a sucrose subprofile.

24. A process as claimed in claim 1, wherein said solution containing betaine is a sugar beet derived solution.

25. A process as claimed in claim 1, wherein said solution containing betaine is a molasses solution or a crystallization run-off or a solution thereof.

26. A process as claimed in claim 1, wherein said solution containing betaine is a vinasse solution.

27. A process as claimed in claim 26, wherein said vinasse is derived from sugar beet or wheat.

28. A process as claimed in claim 1, wherein said parts are used to substitute 5% to 70% of eluent water.

29. A process as claimed in claim 1, wherein the process provides a betaine fraction with a betaine content of 40% to 98% on DS.

30. A process as claimed in claim 1, wherein the process provides a betaine yield in a range of 60% to 98% on the basis the betaine in the betaine-containing feed solution.

31. A process as claimed in claim 1, wherein the process provides a sucrose fraction with a sucrose content of 88% to 98% on DS.

32. A process as claimed in claim 1, wherein the process provides a sucrose yield in a range of 80 to 98% on the basis of the sucrose in the sucrose-containing feed solution.

33. A process as claimed in claim 1, wherein said one or more parts of a separation profile are introduced to one or more eluent introduction positions within the same separation system or to one or more eluent introduction positions in other similar parallel separation systems or in different separation systems.

* * * * *